United States Patent [19]

Wivell

[11] Patent Number: 5,525,344
[45] Date of Patent: Jun. 11, 1996

[54] CLEAR COLD CREAM COSMETIC COMPOSITIONS

[75] Inventor: Susan C. Wivell, Madison, Conn.

[73] Assignee: Chesebrough-Pond's USA Co., Division of Conopco, Inc., Greenwich, Conn.

[21] Appl. No.: 367,647

[22] Filed: Jan. 3, 1995

[51] Int. Cl.⁶ ................................................ A61K 7/02
[52] U.S. Cl. .................... 424/401; 424/78.03; 514/846
[58] Field of Search ......................... 424/401, 78.03; 514/846

[56] References Cited

U.S. PATENT DOCUMENTS

| | | | |
|---|---|---|---|
| 4,806,572 | 2/1989 | Kellett | 424/401 |
| 5,011,681 | 4/1991 | Ciotti et al. | 424/81 |
| 5,160,739 | 11/1992 | Kanga | 424/401 |
| 5,302,382 | 4/1994 | Kasprzak | 424/401 |
| 5,332,569 | 7/1994 | Wood et al. | 424/401 |
| 5,340,570 | 8/1994 | Wong et al. | 424/401 |
| 5,387,417 | 2/1995 | Kentsch | 424/401 |
| 5,439,682 | 8/1995 | Wivell et al. | 424/401 |

*Primary Examiner*—Robert E. Sellers
*Attorney, Agent, or Firm*—Milton L. Honig

[57] ABSTRACT

A clear cold cream cosmetic composition is provided that includes, water, a $C_2$–$C_6$ polyhydric alcohol, a poly ($C_2$–$C_4$ alkoxylate) polymer, a volatile $C_{10}$–$C_{20}$ hydrocarbon and a silicone emollient system. These compositions exhibit visual clarity with excellent make-up and grease removal properties with superior, nongreasy skinfeel.

4 Claims, No Drawings

CLEAR COLD CREAM COSMETIC COMPOSITIONS

BACKGROUND OF THE INVENTION

1. Field of the Invention

The invention concerns non-classical cold cream cosmetics that are clear and exhibit improved make-up removal efficacy.

2. The Related Art

Modern cleansing creams are based on the solvent action of mineral oil to remove through binding either grime or make-up from skin. Removal of pigments of rouge, lipstick and face powder is a daily problem for most women. Cleansing creams have proved the ideal agent to perform this function.

Historically cleansing creams evolved over a period of centuries. Galen, a Greek physician around the year 150, is reported to be the inventor of the first cold cream. Skin preparations of that period consisted of animal and vegetable fats and oils. Beeswax and olive oil were the prime ingredients. Galen conceived the idea of incorporating water into a molten mixture of beeswax and olive oils. In the resultant product, the emollient effect of oil was accelerated, and a pleasant cooling effect was obtained from evaporation of water. Unfortunately the process of manufacture was slow and laborious. Products were also unstable and subject to developing rancidity. In time, sweet almond oil replaced the olive oil of the older formulations. Borax was introduced to cut manufacturing time, and a whiter and more stable emulsion resulted.

A cold cream can be classified as a form of cleansing cream but with a heavier body. These products were originally described as "refrigerans", latin for "making cold", because when applied they create a cooling sensation. Until early this century, many druggists would compound their own Ointment of Rose Water and keep it fresh on ice, hence, "cold" skin cream. The dictionary describes cold cream as a soothing and cleansing cosmetic or a cosmetic, typically of oily and heavy consistency, used to soothe and cleanse the skin. Classic cold cream is one containing the components beeswax, mineral oil, water and borax. Interest has arisen in non-classical forms of cold cream, especially those that combine enhanced aesthetics with efficacy.

Accordingly, it is an object of the present invention to provide a cosmetic composition which is a clear (transparent) product retaining many of the physical attributes of the traditional opaque cold creams.

It is another object of the present invention to provide a cosmetic composition having superior skinfeel (non-greasy) and grease, makeup removal and cleansing efficacy comparable to traditional cold cream.

These and other objects of the present invention will become more readily apparent through the following summary and detailed description.

SUMMARY OF THE INVENTION

A clear cold cream cosmetic composition is provided that includes:

(i) from about 1 to about 50% by weight of water;

(ii) from about 1% to about 60% by weight of a $C_2$–$C_6$ polyhydric alcohol;

(iii) from about 1 to about 50% by weight of a poly ($C_2$–$C_4$ alkoxylate) polymer;

(iv) from about 0.1 to about 40% by weight of a $C_{10}$–$C_{20}$ hydrocarbon; and (v) from about 0.1 to about 30% by weight of a silicone emollient.

DETAILED DESCRIPTION OF THE INVENTION

It has been discovered that a clear composition with excellent make-up and grease removability can be achieved by combining a volatile $C_{10}$–$C_{20}$ hydrocarbon in an aqueous emulsion with a $C_2$–$C_6$ polyhydric alcohol, a poly ($C_2$–$C_4$ alkoxylate) polymer, and a silicone oil emollient system. In particular, compositions of the present are water-in-oil emulsions, with the external oil phase operating to achieve the cold cream cleansing effect for make-up and grease removal. The oil phase should preferably constitute from about 5 to less than 50%, more preferably 10 to 30%, optimally from 12 to 18% by weight of the total composition. Thickening and transparency is achieved by utilizing a high level of internal aqueous phase. Amounts of the aqueous phase will be at least 50%, preferably between 70 and 90% by weight of the composition.

Compositions of the present invention are intended to be optically clear cosmetic products with the ability to be packaged in a clear container. These compositions are intended to preferably have a refractive index of 1.3975 to 1.4200 at 21° C., an optical clarity better than 50 NTU (Nephelometric Turbidity Units) at 21° C. and a viscosity of at least 10,000 cps, preferably at least 30,000 cps at 21° C. The refractive indices (measured at 5891° A) of the water and oil phases should match within 0.0050, preferably within 0.0004 refractive index units. An optically clear cold cream of the present invention should be one that is visually clear, and, like glass, allows ready viewing of objects behind it. Preferably, the compositions will have a turbidity measurement of less than 30 NTU. Distilled water has a turbidity of 0 NTU and whole milk diluted 1 part in 350 parts of distilled water has a turbidity of 200 NTU.

Water is an essential element of the aqueous phase of compositions according to the present invention. Amounts of water may range from about 1 to about 50%, preferably from about 10 to about 35%, optimally from about 15 to about 30% by weight.

Another component of the aqueous phase of compositions according to the present invention is a polyhydric alcohol containing from 2 to 6 hydroxyl groups, preferably from 2 to 3 hydroxyl groups. The alcohol may also contain from 2 to 6 carbon atoms, preferably from 2 to 3 carbon atoms. Suitable polyhydric alcohols include ethylene glycol, propylene glycol, trimethylene glycol, glycerin and sorbitol. Most preferred is propylene glycol. Amounts of the polyhydric alcohol may range from about 1 to about 60%, preferably from about 10 to about 50%, optimally from about 25 to about 35% by weight of the total composition.

A further component of the aqueous phase of compositions according to the present invention is that of a poly ($C_2$–$C_4$ alkoxylate) polymer. This polymer will contain from 3 to 200 units of $C_2$–$C_4$ alkylene oxide monomer units. These units may either be homopolymerized, copolymerized with another alkylene oxide monomer unit, or condensed with an organic hydrophobe such as a $C_2$–$C_{20}$ alkanoic acid or alcohol. Illustrative homo-and co-polymers are polyethylene glycol, polypropylene glycol and poly(ethylene oxide)(propylene oxide) (commercially available from the BASF Corporation under the Pluronic trademark). Illustrative of those with hydrophobe units are PPG-15 stearyl ether, PEG-10 stearyl ether, PPG-15 palmityl ether and Poloxamine 1307 (commercially available from the BASF Corporation under the Tetronic® 1307 trademark). Most preferred is polyethylene glycol, especially PEG 5, PEG 32, PEG 400 and combinations thereof. Amounts of the poly ($C_2$-$C_4$ alkoxylate) polymer will range from about 1 to about 50%, preferably from about 10 to about 30%, optimally from about 15 to about 25% by weight of the total composition.

Preservatives can also be incorporated in amounts effective to protect against growth of potentially harmful microorganism in cosmetic compositions according to the present invention. Preferably they are added to the aqueous phase, but some may be added to the oil phase. Levels of such preservatives may range from about 0.001 to about 1% by weight. Illustrative preservatives are methyl paraben, propyl paraben, imidazolidinyl urea, sodium dehydroxyacetate and benzyl alcohol. Other minor adjunct ingredients may also be included such as fragrances, electrolytes and colorants, each in their effective amounts to accomplish their respective functions.

The oil phase of emulsion compositions according to the present invention ordinarily will comprise a mixture of volatile hydrocarbon and silicone materials.

Accordingly, compositions of the present invention in the oil phase will contain a volatile $C_{10}$-$C_{20}$ saturated or unsaturated, branched or unbranched chain hydrocarbon. Illustrative commercially available unsaturated, unbranched hydrocarbons are α-olefins such as 1-decene, 1-dodecene, 1-tetradecene, 1-hexadecene and mixtures thereof. Illustrative of commercially available branched hydrocarbons are isodecane, isododecane, isohexadecane and combinations thereof. The branched hydrocarbons are sold by Presperse Inc. (South Plainfield, New Jersey) under the trademark Permethyl®. Concentration of the hydrocarbon will range from about 0.1 to about 40%, preferably from about 1 to about 20%, optimally from about 4 to about 8% by weight.

Silicone oils will constitute from about 0.1 to about 30%, preferably from about 1 to about 20%, optimally from about 5 to about 15% by weight of the total composition. These silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. The linear types are known by the CTFA name dimethicone while the cyclic types are known by the CTFA name of cyclomethicone. The cyclomethicones are commercially available from Dow Corning under the trademark DC 344 and DC 345.

Nonvolatile silicone oils useful in compositions of the present invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Preferred polydimethyl siloxanes are those having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company).

For purposes of this invention, most advantageous is the use of a combination of cyclomethicone, dimethicone copolyol and dimethiconol. In particular, it is desirable to use a combination of DC 3225C, DC 1401 and DC 1418. Dow Corning 3225C is a mixture of cyclomethicone-dimethicone Copolyol silicone fluid having a viscosity at 25° C. of 100–1,000 cst and a specific gravity at 25° C. of about 0.963. Amounts of this particular silicone will be present from about 1 to about 10% of the total composition. Dow Corning 1401 is a blend of cyclomethicone and dimethiconol having a viscosity at 25° C. of 5,000–7,000 cst and a specific gravity at 25° C. of about 0.960. Amounts of DC 1401 may range from about 0.5 to about 10%, preferably from about 2 to about 6% by weight of the total composition. Dow Corning 1418 is a blend of dimethicone and a silicone gum having a viscosity at 25° C. of 350,000–750,000 cst and a specific gravity at 25° C. of about 0.970. Amounts of the DC 1418 will range from about 0.1 to about 10%, preferably from about 0.5 to about 5% by weight of the total composition.

The following examples will more fully illustrate select embodiments of this invention. All parts, percentages and proportions referred to herein and in the appended claims are by weight unless otherwise indicated.

EXAMPLE 1

A first variant clear gel composition of the present invention is described below.

TABLE I

| Medium Viscosity Variant Clear Gel Formula | |
|---|---|
| COMPONENT | WEIGHT % |
| Water Phase | |
| Water | 19.76 |
| Witch Hazel | 16.41 |
| Propylene Glycol | 14.76 |
| Glycerin | 12.30 |
| PEG 5/PEG 32 | 11.48 |
| PEG 400 | 8.20 |
| Sodium Chloride | 0.41 |
| Oil Phase | |
| Isododecane | 7.03 |
| dimethicone-Fluid Blend (DC 1401) | 4.57 |
| cyclomethicone dimethicone Copolyol (DC 3225C) | 3.52 |
| dimethicone-gum Blend (DC 1418) | 1.55 |

EXAMPLE 2

Another variant clear gel formulation of the present invention, thicker than that of Example 1, is described below.

TABLE II

| High Viscosity Variant Clear Gel Formula | |
|---|---|
| COMPONENT | WEIGHT % |
| Water Phase | |

TABLE II-continued

High Viscosity Variant Clear Gel Formula

| COMPONENT | WEIGHT % |
|---|---|
| Water | 32.67 |
| PEG 5/PEG 32 | 18.76 |
| Propylene Glycol | 16.41 |
| Glycerin | 15.01 |
| Glydant Plus ® | 0.09 |
| Oil Phase | |
| cyclomethicone/dimethicone copolyol (DC 3225 C) | 6.28 |
| Isohexadecane | 4.36 |
| dimethicone-fluid Blend (DC 1401) | 3.96 |
| dimethicone-gum Blend (DC 1418) | 2.36 |
| Fragrance | 0.09 |

EXAMPLE 3

Another variant clear gel formulation of the present invention is described below. This gel is more fluid than that reported for Example 2.

TABLE III

Low Viscosity Variant Clear Gel Formula

| COMPONENT | WEIGHT % |
|---|---|
| Water Phase | |
| Propylene Glycol | 17.48 |
| Water | 16.65 |
| Witch Hazel | 16.65 |
| Glycerin | 12.49 |
| PEG 5/PEG 32 | 11.65 |
| PEG 400 | 8.32 |
| Glydant Plus ® | 0.08 |
| Oil Phase | |
| Isododecane | 9.29 |
| dimethicone-fluid Blend (DE 1401) | 3.29 |
| cyclomethicone/dimethicone copolyl (DC 3225C) | 3.29 |
| dimethicone-gum Blend (DC 1418) | 0.80 |

EXAMPLE 4

This Example details the results of an in-vitro method assessing comparative make-up removal efficacy of formulations according to the present invention. The method utilized a collagen substrate which closely mimics skin in composition, topography, surface tension, pH and ionic strength. This collagen substrate is IMS R-11 Vitro Skin which was formed into rectangular areas of 2 by 3 centimeter sites, marked off for use by an indelible marker on the reverse side of the skin.

After marking, the color of the skin was measured using a Minolta ChromaMeter CR-100 to give a set of baseline readings (A). The 3-dimensional color coordinate system L*a*b* was utilized and each recorded result was the average of three individual measurements. The designated areas were then coated with 0.25 grams of Elizabeth Arden® Flawless Finish liquid make-up spread evenly with a fingercot. After drying, a second color measurement was performed (reading B).

The skin was then cut into 2-site pieces for each sample formulation. To each site was applied 0.10 grams of the test cleanser formulation. Thereafter, the skin was transferred to a damp sponge and the formulation rubbed over each site for 20 seconds. The sites were then gently wiped with tissue and the skin placed into a beaker of warm water for 20 seconds. Upon removal and gentle drying, a final color reading (reading C) was recorded as the average of three individual measurements.

The percentage removal was calculated as:

$$\frac{B-C}{B-A} \times 100$$

where $$B - A = \sqrt{(L_B - L_A)^2 + (a_B - a_A)^2 + (b_B - b_A)^2} \quad \text{etc.}$$

The following two formulations were prepared and then performance compared against traditional Pond's® Cold Cream.

TABLE IV

| | WEIGHT % | |
|---|---|---|
| COMPONENT | 1 | 2 |
| Water Phase | | |
| Water | 33.23 | 33.23 |
| Polyethylene Glycol | 19.97 | 19.97 |
| Glycerin | 12.48 | 12.48 |
| Propylene Glycol | 17.47 | 17.47 |
| Glydant Plus ® | 0.10 | 0.10 |
| Oil Phase | | |
| Isohexadecane | 4.63 | — |
| dimethicone fluid | 2.71 | 7.34 |
| dimethicone gum | 2.52 | 2.52 |
| Fragrance | 0.10 | 0.10 |

TABLE V

IN-VITRO MAKE-UP REMOVAL RESULTS

| % MAKE-UP REMOVED | FORMULATION |
|---|---|
| 91.0 | Pond's Cold Cream |
| 80.4 | No. 1 |
| 67.5 | No. 2 |

From the results seen in Table V, it is evident that partial replacement of the silicone fluid with isohexadecane achieved a significant increase in the amount of make-up removed. Formulation 1 exhibited a make-up removal efficacy very close to that of traditional cold cream even though it was clear in appearance and did not contain beeswax/borax or mineral oil (a combination known for grease and makeup removal).

The foregoing description and Examples illustrates selected embodiments of the present invention. In light thereof, various modifications will be suggested to one skilled in the art, all of which are within the spirit and purview of this invention.

What is claimed is:

1. A clear cold cream cosmetic composition having an optical clarity of better than 50 NTU at 21° C. comprising:
   (i) from about 1 to about 50% by weight of water;
   (ii) from about 1% to about 60% by weight of a $C_2$–$C_6$ polyhydric alcohol;
   (iii) from about 1 to about 50% by weight of a poly ($C_2$–$C_4$ alkoxylate) polymer;

(iv) from about 0.1 to about 40% by weight of isohexadecane; and (v) from about 0.1 to about 30% by weight of a silicone emollient comprising:

(a) from about 1 to about 10% by weight of a cyclomethicone-dimethicone copolyol silicone fluid mixture having a viscosity at 25° C. of 100 to 1,000 cst; and (b) from about 0.5 to about 10% by weight of a blend of cyclomethicone and dimethiconol.

2. A composition according to claim 1 which is a water-in-oil emulsion with an aqueous phase that is at least 50% by weight of the total composition.

3. A composition according to claim 1 which is a water-in-oil emulsion with an aqueous phase from 70 to 90% and an oil phase from about 5 to less than 50% by weight of the total composition.

4. A composition according to claim 1 wherein the silicone emollient further comprises from about 0.5 to about 5% by weight of a blend of dimethicone and a silicone gum having a viscosity at 25° C. of 350,000 to 750,000 cst.

* * * * *

UNITED STATES PATENT AND TRADEMARK OFFICE
CERTIFICATE OF CORRECTION

PATENT NO. : 5,525,344
DATED : June 11, 1996
INVENTOR(S) : Wivell

It is certified that error appears in the above-indentified patent and that said Letters Patent is hereby corrected as shown below:

Claim 1, replace

"(v) from about 0.1 to about 30% by weight of a silicone emollient comprising:
   (a) from about 1 to about 10% by weight of a cyclomethicone-dimethicone copolyol silicone fluid mixture having a viscosity at 25°C. of 100 to 1,000 cst; and
   (b) from about 0.5 to about 10% by weight of a blend of cyclomethicone and dimethiconol"

with

--(v) from about 1 to about 10% by weight of a cyclomethicone-dimethicone copolyol silicone fluid mixture having a viscosity at 25°C of 100 to 1,000 cst; and (vi) from about 0.5 to about 10% by weight of a blend of cyclomethicone and dimethiconol. --

Signed and Sealed this

Eighth Day of April, 1997

Attest:

BRUCE LEHMAN

*Attesting Officer*     *Commissioner of Patents and Trademarks*